United States Patent [19]

Daniels

[11] Patent Number: 4,689,833
[45] Date of Patent: Sep. 1, 1987

[54] WEIGHT LIFTING BELT

[76] Inventor: Jerry Daniels, 4308 Ooltewah-Ringgold Rd., Ooltewah, Tenn. 37363

[21] Appl. No.: 840,132

[22] Filed: Mar. 17, 1986

[51] Int. Cl.$^4$ ............................. A41F 9/00; A61F 5/24
[52] U.S. Cl. ............................................. 2/322; 2/338; 2/243 B; 128/78; 128/95.1
[58] Field of Search ............... 2/321, 322, 338, 243 B; 128/78, 95, 133, 134, 69, 75; 272/143, 144

[56] References Cited

U.S. PATENT DOCUMENTS

| | | | |
|---|---|---|---|
| 802,558 | 10/1905 | Gaisman | 2/338 X |
| 1,792,158 | 2/1931 | Gleckner | 2/322 X |
| 1,944,646 | 1/1934 | McMurray | 2/322 X |
| 1,973,646 | 9/1934 | Mix | 2/338 X |
| 2,908,015 | 10/1959 | Epstein | 2/322 |
| 4,348,774 | 9/1982 | Woodson | 2/338 |
| 4,545,370 | 10/1985 | Welsh | 2/338 |

FOREIGN PATENT DOCUMENTS

| | | | |
|---|---|---|---|
| 1083167 | 6/1954 | France | 2/322 |
| 26545 | 2/1984 | Japan | 2/338 |

*Primary Examiner*—Stephen Marcus
*Assistant Examiner*—T. Graveline
*Attorney, Agent, or Firm*—Alan Ruderman

[57] ABSTRACT

A weight lifting belt produced from two strips of leather, one strip being substantially elongated relative to the other and having an enlarged width over a portion thereof intermediate first and second narrow end portions, the first end portion being substantially longer than the second end portion. The other strip comprises a short section having surfaces folded back on itself to form a fold and a pair of ends. The ends being secured to the shorter end portion of the elongated strip and a buckle being entrapped between the surfaces of the fold. The first end portion of the long strip has holes for receiving the tongue or tongues of the buckle. The method for producing the belt includes cutting a blank of the longer strip in a staggered relationship in a hide relative to adjacent blanks so that each wide portion of one blank of the longer strip is disposed adjacent a narrow portion of the blank forming the adjacent strips. The second strips are also cut from the hide, folded about respective buckles and secured to the short end of the first strip.

10 Claims, 5 Drawing Figures

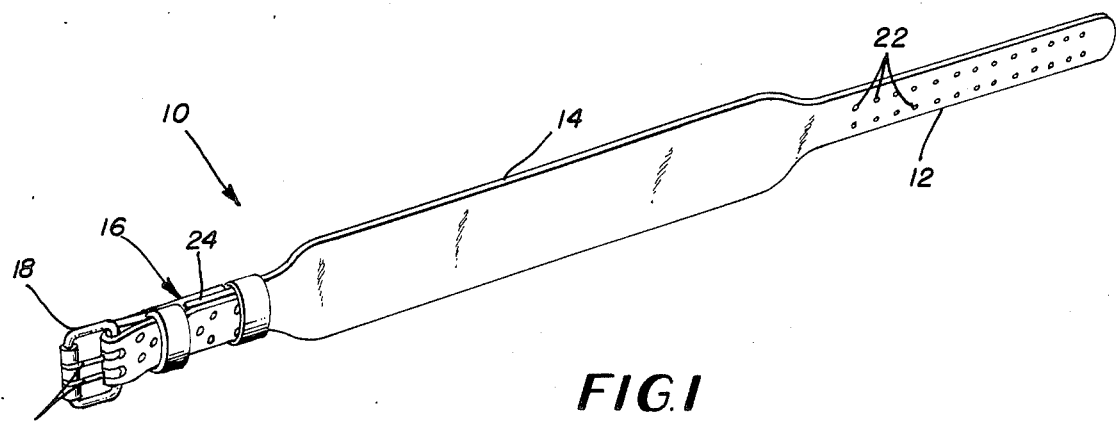
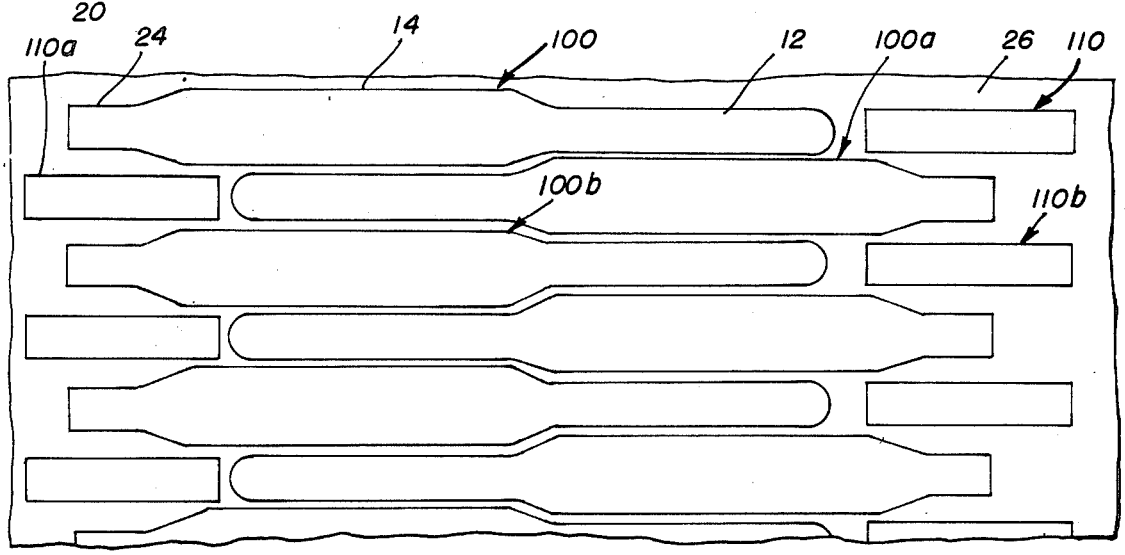
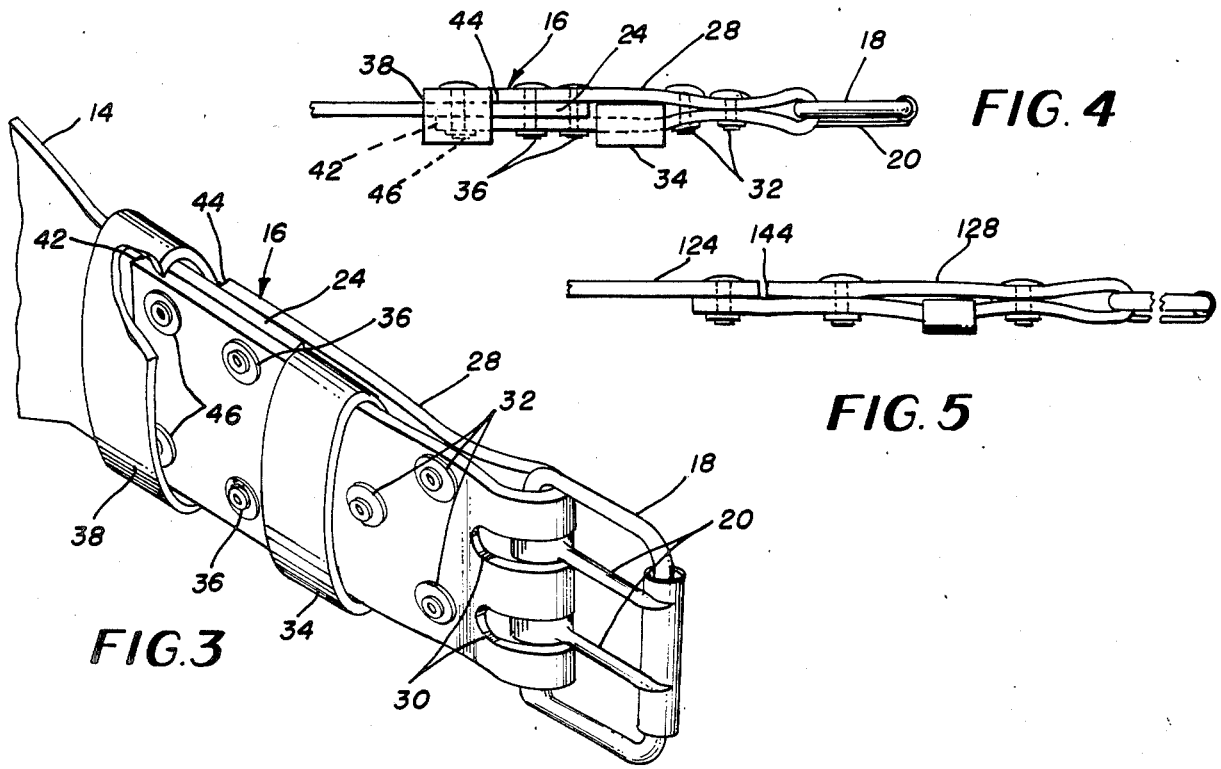

WEIGHT LIFTING BELT

BACKGROUND OF THE INVENTION

This invention relates to leather belts and more particularly to a leather belt utilized by weight lifters and body builders, the belt having a two piece construction permitting an increase in the yield of belts produced from a given hide.

Weight lifting belts are designed to have enlarged widths extending from the front of the pelvic or hip bones to, and including, the back portion relative to the connecting elements at the front of the body of a wearer. This design provides substantial support to the back while precluding discomfort and mobility at the front of the wearer. Thus, such belts, when ope and elongated have a wide central portion with narrow end portions, one end carrying the buckle with one or more tongues and the other other end carrying the cooperating tongue receiving fastening holes. Such belts are constructed of top grain leather for withstanding large forces placed on them by the abdominal muscles of a weight lifter when lifting great amounts of weight.

Conventionally, these belts are constructed from a single strip of leather cut by a die from a hide, the strip being elongated a greater amount than the required usable length of the belt so that one end portion can be folded back upon itself for securing the buckle between adjacent plies. The end which is folded back is thereafter secured to the adjacent ply by rivets or the like to secure the buckle in place. In otherwords, conventional weight lifting belts are constructed in a manner similar to dress or casual belts despite the widened central portion.

Generally, the width of the central portion of these belts is four to six inches with the end portion being approximately two to two and one half inches. The part of the hide from which the belts are cut obviously vary in size dependent upon the cow or steer from which the part of the hide is taken. Generally such hides range in size from approximately 54 to 60 inches along one side edge and approximately 26 to 30 inches along the other side edge. The belt is then cut having its axis of elongation extending from one of the shorter edges to the other. Thus, for an average hide approximately six conventional four inch wide belts can be produced while four conventional six inch wide belts can be produced as a certain amount of wasted hide is necessary for cuts made between adjacent belts due to the width of the dies. Clearly, if more belts can be cut from a given hide, the cost for producing each belt is reduced accordingly.

SUMMARY OF THE INVENTION

Consequently, it is a primary object of the present invention to provide a leather weight lifting belt having a construction permitting an increase in the number of belts produced from a given hide relative to the known constructions.

It is another object of the present invention to provide a method for producing leather weight lifting belts having greater production yields from a given hide than heretofore obtainable.

It is a further object of the present invention to provide a weight lifting belt constructed from two strips of leather, one of the strips being substantially elongated relative to the other and having an enlarged width over a portion thereof intermediate a first narrow end portion and a second narrow end portion, the first end portion being substantially longer than the second end portion, and the other strip being a shorter section having surfaces folded back on itself to form a loop and a pair of ends, the loop acting to entrap a buckle and the end being secured to the second end portion of the elongated strip.

It is a yet further object of the present invention to provide a method of producing a plurality of leather weight lifting belts each having central portions of enlarged width compared to the end sections, each belt comprising two strips of leather, a first of the strips being elongated relative to the other and containing the wider portion, the first strips of the belt being cut as a blank in a hide by staggering adjacent belt blanks such that the wide portion of each blank in the hide is adjacent a narrow portion of adjacent blanks so that a given hide can produce a greater yield of belts.

Accordingly, the present invention provides a leather weight lifting belt and a method for producing same, the belt having two strips of leather, one strip being substantially elongated relative to the other and having an enlarged width over a portion thereof intermediate a first narrow end portion and a second narrow end portion, the first end portion being substantially longer than the second end portion. The other strip comprises a short section having surfaces folded back on itself to form a folded loop and a pair of ends, the loop acting to entrap a buckle and the ends being secured to the shorter end portion of the elongated strip. Preferably, the second end is lapped between and secured to the ends of the short section. The first end portion of the long strip has buckle connecting holes for receiving at least one buckle tongue.

With a belt constructed in this manner the shorter strip can be of a standardized or fixed size, while the longer strip can be of a length required for the waist size of the various users. Since the longer strip is of a substantially shorter size than one constructed from a single strip of leather, the dies which are used for cutting the strip may be spaced at various distances from the edges of the hide from which the belts are cut. Consequently, the wide portion of the belt may be cut from the hide in a staggered arrangement wherein each blank of leather forming the longer strip may have the wide portion of the belt disposed adjacent the long narrow portion of the adjacent blanks thereby permitting additional blanks and belts to be formed from a given hide than with prior art constructions. For example, eight 4 inch belts can be produced from a hide that previously produced six such belts and six 6 inch belts can be produced from a hide previously producing four belts. Thus, the method includes positioning each cutting die on the hide to cut a blank of the longer strip in staggered relationship with those of adjacent blanks, each wide portion of the blank of strip being disposed adjacent a narrow portion of the blank forming the next adjacent strip; cutting the second strips from the hide; folding the second strips about respective buckles to entrap same; and securing the ends of each of the second strips to a respective one of the short ends of the first strip.

BRIEF DESCRIPTION OF THE DRAWINGS

The particular features and advantages of the invention as well as other objects will become apparent from the following description taken in connection with the accompanying drawings, in which:

FIG. 1 is a perspective view of a weight lifting belt constructed in accordance with the principles of the present invention;

FIG. 2 is a plan view of a portion of a typical leather hide from which belt blanks are formed in accordance with the invention, and illustrating the disposition of the dies for cutting respective blanks in the hide;

FIG. 3 is an enlarged fragmentary perspective view of the buckle and of the belt illustrated in FIG. 1, with parts thereof broken away;

FIG. 4 is a a top plan view of the elements illustrated in FIG. 3; and

FIG. 5 is a top plan view of a modification of the belt illustrated in FIG. 1.

DESCRIPTION OF THE PREFERRED EMBODIMENTS

Referring now to the drawings, a weight lifting belt constructed in accordance with the principles of the present invention is illustrated generally at 10, the belt having a first elongated section 12 at one end thereof of relatively narrow width smoothly expanding in width to a central section 14 forming a substantial portion of the belt and then smoothly contracting into another section 16 of a relatively narrow width at the other end thereof which is shorter than the section 12. The central section 14 is of a length such as to fit about the back of a wearer and extend toward each of the front pelvic or hip bones. The end section 16 carries a buckle 18 having at least one and preferably two tongues 20 which cooperate with tongue receiving holes 22 in the other end section 12 for adjustably fastening the ends about the wearer.

As aforesaid, the end portion 16 of conventional belts are constructed from the same single strip of material from which the sections 12 and 14 would be formed so that the length of the blank from which the belt is constructed is equal to the combined length of the sections 12 and 14 plus a length substantially twice that of the front section 16, the latter length being folded for receiving the tongue holding portion of the buckle and having slots through which the tongues extend. Thus, the length of most conventional belts of this type require a blank of leather of a length in a range of approximately 42 to 54 inches providing only a small margin at the side edges of a hide from which it is cut. Consequently, the wide central portion of the belt is the sole determinant of the number of blanks which can be cut from a given hide. For example, for a belt having a six inch width across the section 14 only four belts can be cut from a standard part of the hide of approximately 28 inch width since a certain amount of space between the belt blanks is wasted due to the thickness of the cutting dies.

The present invention, on the otherhand, provides a belt wherein section 16 comprises a small extended portion 24, e.g., approximately two inches of the strip containing sections 12 and 14, with the remainder of section 16, including the folded buckle receiving portion, being formed from a second strip of leather. As illustrated in FIG. 2, a leather hide 26 therefore may have blanks cut in a staggered manner such as blanks 100, 100a, 100b, etc., the blanks being cut in the hide by staggering cutting dies having the desired blank configuration. The configuration of the blank is that of the sections 12 and 14 of the belt plus the small extended portion 24 at the end remote from the elongated portion 12. The length of the blank ranges from approximately 31 inches to 39 inches and by staggering the blanks the wide portions 14 can overlie adjacent narrow portions 12 thereby reducing the amount of hide required in the lengthwise direction of the hide, i.e, the direction of adjacent blanks, as clearly illustrated in FIG. 2.

The second strip of material required to form the remainder of section 16 may be cut as blanks from the hide at any convenient location, and thus these blanks illustrated in FIG. 2 at 110, 110a, 110b, etc., may be disposed adjacent the end section 12 of the respective elongated blanks to which they are to be fastened. It should be understood that a greater yield of belts may thus be produced from a given hide than heretofore possible in the prior art since the elongated end section 12 is approximately two to two and one half inches compared to the four to six inch width of the widened central portions.

As illustrated in FIGS. 3 and 4, each blank 110, 110a, 110b, etc., is formed to form a buckle securing end 28 of the belt and fastened to the small portion 24 extending at the end of the wide section 14 remote from the portion 12. Slots 30 are cut in the folded portion for receiving the tongues 20 of the buckle 18 and rivets 32 securely fasten the two plies of the second strip together to lock the buckle in place. Preferably a leather securing loop 34 is inserted between the plies of the end 28 adjacent the rivets 32 and the ends of the second strip forming the end 28 are riveted together by rivets 36 with the portion 24 sandwiched therebetween, the rivets 36 extending through the three plies. Thus, the full length of the belt 10 is formed by the two stips. Another leather securing loop 38 preferably is also riveted to the buckle end 16 by rivets 46. In order to hide the front joint as well as providing a comfortable step-down against the body of a wearer and to avoid the use of rivets 46 having an unnecessarily long length, the front edge 42 of the strip forming the end 28 is offset from the rear edge 44 by a small amount. Thus, the rivets 46 may extend through only the three plies forming the front of the short strip, the portion 24 of the long strip and the rear of the loop 38 rather than four plies were it not for the offset.

In FIG. 5 there is illustrated another embodiment of the belt formed by the method of the present invention wherein the rear edge 144 of the second strip forming the buckle end 128 substantially abuts the leading edge of the short portion 124 of the long strip forming the remainder of the belt so that only one ply of the short strip is riveted to the long strip. Although this construction does not provide the strength of the construction illustrated in the first embodiment, it is adapted for use by children where the loading on the belt is minimal.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A weight lifting belt comprising a pair of strips of natural leather, one of said strips being longitudinally elongated and having a central portion intermediate first and second end portions, said central portion having a larger width relative to both end portions, said central portion and a first of said end portions being substantially elongated longitudinally relative to the second end portion, the other strip of said pair of strips comprising a short strip relative to said one strip and having substantially the same width as said second end portion, a fold formed in said other strip so that terminal ends thereof are substantially adjacent end other and a surface of said other strip forms superposed opposed surfaces, a buckle entrapped intermediate said opposed surfaces at said fold, and connecting means for fixedly securing said second end portion to said other strip remote from said buckle, said buckle and said first end portion having cooperating fastening means for adjustably attaching said buckle to said first end portion, one terminal end portion of said other strip being offset from the other terminal end portion relative to said fold, and said second end portion is in abutment and secured to one surface of said opposed surfaces, said one surface being adjacent the terminal end most remote from said fold.

2. A weight lifting belt as recited in claim 1, wherein said connecting means comprises rivets extending through said second end portion and said other strip.

3. A weight lifting belt comprising a pair of strips of natural leather, one of said strips being longitudinally elongated and having a central portion intermediate first and second end portions, said central portion having a larger width relative to both end portions, said central portion and a first of said end portions being substantially elongated longitudinally relative to the second end portion, the other strip of said pair of strips comprising a short strip relative to said one strip and having substantially the same width as said second end portion, a fold formed in said other strip so that terminal ends thereof are substantially adjacent each other and a surface of said other strip forms superposed opposed surfaces, a buckle entrapped intermediate said opposed surfaces at said fold, and connecting means for fixedly securing said second end portion to said other strip remote from said buckle, said buckle and said first end portion having cooperating fastening means for adjustably attaching said buckle to said first end portion, said second end portion being sandwiched in abutment with and secured to said opposite surface, one terminal end of said other strip being offset from the other terminal end relative to said fold, and a leather retaining loop disposed in abutment with said second end portion, said loop having a finite width in the direction of the longitudinally elongated direction of said belt, one edge of said loop being disposed adjacent the terminal end most adjacent said fold, and means for securing one ply of said loop to said second end portion and to said other strip adjacent the terminal end most remote from said fold and with a portion of the width of the loop overlaying the terminal end most remote from the fold.

4. A weight lifting belt as recited in claim 3, wherein said last mentioned means comprises rivets extending through said one ply of said loop and through said second end portion.

5. A weight lifting belt as recited in claim 4, wherein said connecting means comprises rivets extending through said second end portion and said other strip.

6. A method of manufacturing longitudinally elongated leather weight lifting belts, each belt having a central portion of greater width than adjacent end portions, said end portions adapted to be adjustably connected together when the belt is worn, said method comprising cutting from a single hide of natural leather two strips of material for each belt, a first of said strips comprising a substantially longitudinally elongated member having said central portion, a first of said end portions adjacent said central portion and a short extended narrow portion of a width equal to the other end portion adjacent the central portion remote from the first of said end portions, the first strip being cut as a blank offset in staggered fashion from adjacent blanks such that the central portion of the blank is adjacent the first end portion of adjacent blanks, the second of said strips comprising a substantially short strip relative to said first strip having a substantially constant width equal to that of said other end portion, the cutting of said second strip being performed in portions of said hide intermediate and adjacent portions of blanks of said first strip, folding the second of said strips to form a fold about a buckle, said buckle having at least one tongue extending through the fold, securing the second strip remote from said fold to the end of the short extended portion of the first strip, and cutting holes in the first of said end portions of the first strip for cooperatively receiving said tongue.

7. In the method as recited in claim 6, wherein the second of said strips is secured to the first strip by disposing said short extended portion of the first strip between adjacent facing surfaces of the second strip to form three plies of the leather and thereafter fastening the three plies together.

8. In the method as recited in claim 7, wherein said fastening comprises riveting the three plies together.

9. In the method as recited in claim 6, wherein the second of said strips is secured to the first strip by offsetting the ends of the second of said strips remote from the fold so that one end extends further from said fold than the other end, and thereafter fastening the short extended portion of the first strip to the second strip adjacent the extended end and fastening facing surfaces of the second strip together adjacent the other end of the second strip.

10. In the method as recited in claim 9, wherein said fastening comprises riveting.

* * * * *